(12) United States Patent
Alheidt et al.

(10) Patent No.: US 9,522,237 B2
(45) Date of Patent: Dec. 20, 2016

(54) POSITIVE DISPLACEMENT FLUSH SYRINGE

(75) Inventors: Thomas Alheidt, Lake Stockholm, NJ (US); Anthony J. Kosinski, New Providence, NJ (US)

(73) Assignee: Becton, Dickinson and Company, Franklin Lakes, NJ (US)

(*) Notice: Subject to any disclaimer, the term of this patent is extended or adjusted under 35 U.S.C. 154(b) by 1910 days.

(21) Appl. No.: 11/031,151

(22) Filed: Jan. 7, 2005

(65) Prior Publication Data

US 2006/0247582 A1    Nov. 2, 2006

(51) Int. Cl.
| A61M 5/315 | (2006.01) |
| A61M 5/50 | (2006.01) |
| A61M 25/00 | (2006.01) |
| A61M 25/10 | (2013.01) |
| A61M 5/14 | (2006.01) |

(52) U.S. Cl.
CPC ......... *A61M 5/31515* (2013.01); *A61M 5/502* (2013.01); *A61M 25/00* (2013.01); *A61M 25/1018* (2013.01); *A61M 2005/1403* (2013.01); *A61M 2005/31508* (2013.01)

(58) Field of Classification Search
CPC ................ A61M 2005/14268; A61M 5/1413; A61M 5/14248
USPC ....................... 604/218, 228, 229
See application file for complete search history.

(56) References Cited

U.S. PATENT DOCUMENTS

| 2,453,591 A | 11/1948 | Poux |
| 2,860,635 A | 11/1958 | Wilburn |
| 3,050,059 A | 8/1962 | Wall et al. |
| 3,331,538 A | 7/1967 | Higgins |
| 3,380,489 A | 4/1968 | Harautuneian |
| 3,478,937 A | 11/1969 | Solowey |
| 3,930,492 A | 1/1976 | Hatsuno et al. |
| 3,987,930 A | 10/1976 | Fuson |
| 4,044,757 A | 8/1977 | McWhorter et al. |
| 4,057,052 A | 11/1977 | Kaufman et al. |
| 4,064,879 A * | 12/1977 | Leibinsohn ........... A61M 5/486 604/121 |
| 4,246,898 A * | 1/1981 | Travalent et al. ............ 604/210 |
| 4,367,738 A | 1/1983 | Legendre et al. |

(Continued)

FOREIGN PATENT DOCUMENTS

| EP | 0 329 358 A2 | 2/1989 |
| EP | 0329358 A2 | 8/1989 |

(Continued)

*Primary Examiner* — Phillip Gray
(74) *Attorney, Agent, or Firm* — Servilla Whitney LLC

(57) ABSTRACT

A flush syringe assembly comprises a barrel including a cylindrical side wall having an inside surface defining a chamber for retaining fluid, an open proximal end and a distal end having a passageway therethrough in fluid communication with the chamber. A plunger including an elongate body portion having a stopper at its distal end is provided. The stopper is slidably positioned in fluid-tight engagement with the inside surface of the barrel for driving fluid out of the chamber through the passageway. The stopper includes a distal portion and a proximal portion separated by a spring element and configured to compress when fluid is being driven through the passageway by motion of the plunger and to continue to drive fluid through the passageway after motion of the plunger has stopped.

15 Claims, 11 Drawing Sheets

(56) References Cited

U.S. PATENT DOCUMENTS

| | | | |
|---|---|---|---|
| 4,493,703 A | 1/1985 | Butterfield | |
| 4,642,102 A * | 2/1987 | Ohmori | A61M 5/31555 604/210 |
| 4,731,068 A | 3/1988 | Hesse | |
| 4,781,684 A | 11/1988 | Trenner | |
| 4,826,483 A * | 5/1989 | Molnar, IV | 604/110 |
| 4,840,616 A * | 6/1989 | Banks | 604/110 |
| 4,906,231 A | 3/1990 | Young | |
| 4,915,692 A | 4/1990 | Verlier | |
| 4,950,240 A | 8/1990 | Greenwood et al. | |
| 4,973,310 A | 11/1990 | Kosinski | |
| 4,978,339 A * | 12/1990 | Labouze et al. | 604/110 |
| 5,037,393 A | 8/1991 | Ellgass | |
| 5,059,181 A * | 10/1991 | Agran | 604/110 |
| 5,085,640 A | 2/1992 | Gibbs | |
| 5,090,962 A | 2/1992 | Landry, Jr. et al. | |
| 5,106,372 A | 4/1992 | Ranford | |
| 5,116,320 A | 5/1992 | Lo Duca | |
| 5,120,314 A | 6/1992 | Greenwood | |
| 5,211,629 A | 5/1993 | Pressly et al. | |
| 5,242,405 A | 9/1993 | Howe | |
| 5,250,030 A * | 10/1993 | Corsich | 604/110 |
| 5,304,138 A | 4/1994 | Mercado et al. | |
| 5,308,322 A | 5/1994 | Tennican et al. | |
| 5,322,515 A | 6/1994 | Karas et al. | |
| 5,370,620 A | 12/1994 | Shonfeld | |
| 5,395,339 A | 3/1995 | Talonn et al. | |
| 5,429,610 A * | 7/1995 | Vaillancourt | A61B 5/1416 600/573 |
| 5,496,285 A | 3/1996 | Schumacher et al. | |
| 5,496,288 A | 3/1996 | Sweeney | |
| 5,593,387 A | 1/1997 | Rupp | |
| D383,205 S | 9/1997 | Pagay et al. | |
| 5,795,337 A | 8/1998 | Grimard | |
| 5,807,312 A | 9/1998 | Dzwonkiewicz | |
| 5,807,343 A | 9/1998 | Tucker et al. | |
| 5,807,374 A | 9/1998 | Caizza et al. | |
| 5,814,017 A | 9/1998 | Kashmer | |
| 5,817,064 A | 10/1998 | De Marco et al. | |
| 5,820,603 A | 10/1998 | Tucker et al. | |
| D403,064 S | 12/1998 | Einav et al. | |
| D406,643 S | 3/1999 | Niedospial, Jr. et al. | |
| 5,899,881 A | 5/1999 | Grimard et al. | |
| 5,899,889 A | 5/1999 | Futagawa et al. | |
| 5,985,962 A | 11/1999 | Knors et al. | |
| 6,171,287 B1 | 1/2001 | Lynn et al. | |
| 6,361,524 B1 * | 3/2002 | Odell et al. | 604/187 |
| 2004/0010235 A1 | 1/2004 | Weilbacher et al. | |
| 2004/0176722 A1 * | 9/2004 | Capes et al. | 604/110 |

FOREIGN PATENT DOCUMENTS

| | | |
|---|---|---|
| EP | 1 221 320 | 7/2002 |
| EP | 1221320 A2 | 7/2002 |
| FR | 2 622 804 A1 | 11/1987 |
| FR | 2622804 A1 | 12/1989 |
| GB | 584841 | 1/1947 |
| GB | 2 197 792 A | 11/1986 |
| GB | 2197792 A | 6/1988 |
| WO | WO 95/28978 | 11/1995 |
| WO | WO-95/28978 | 11/1995 |
| WO | WO-98/56440 | 12/1998 |
| WO | WO 98/56440 | 12/1998 |

* cited by examiner

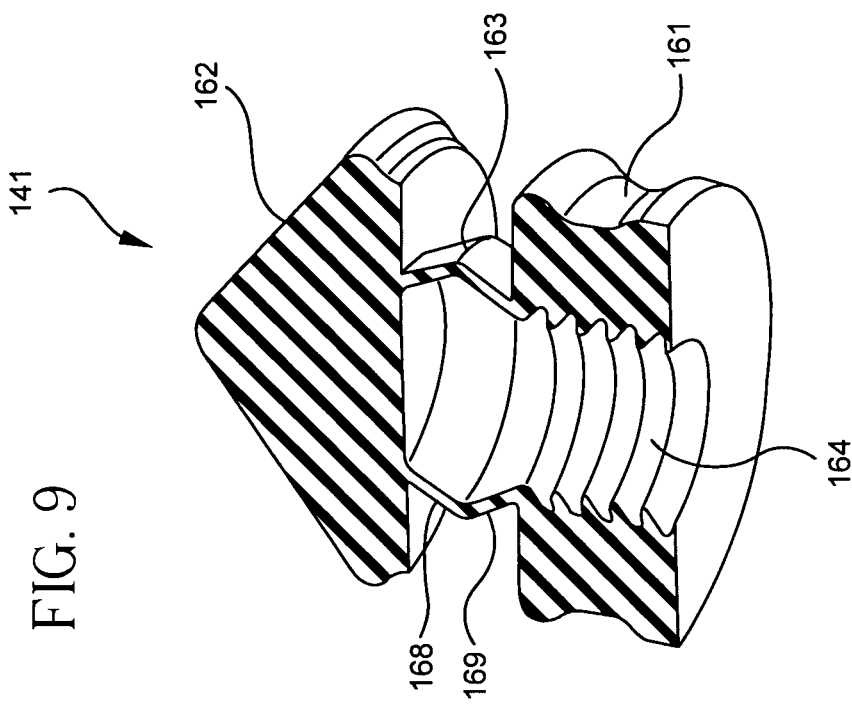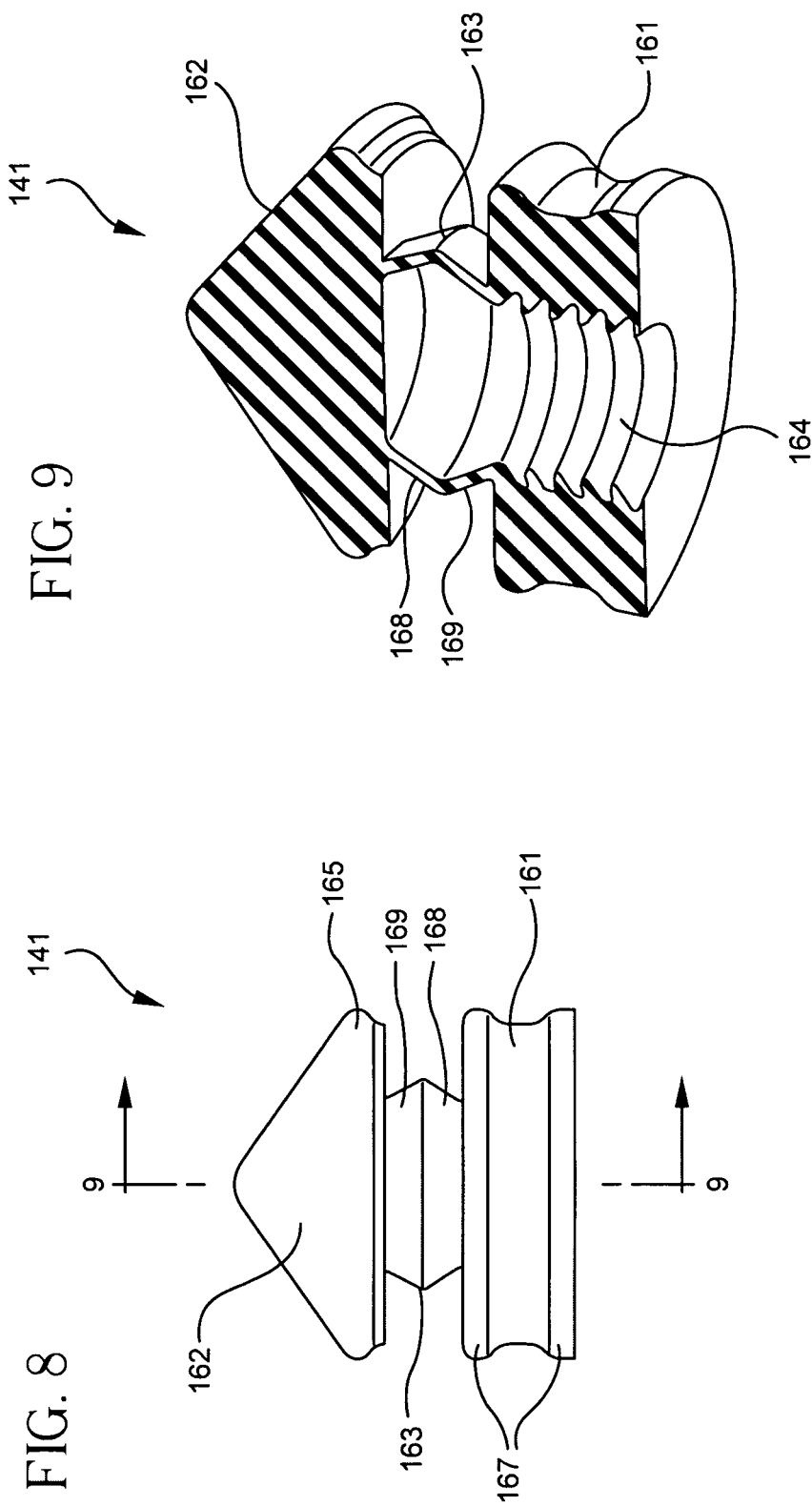

POSITIVE DISPLACEMENT FLUSH SYRINGE

BACKGROUND OF THE INVENTION

The present invention relates to syringe assemblies and particularly to syringe assemblies for use in flush procedures, for vascular access devices (VAD's).

VAD's are commonly used therapeutic devices. There are two general classifications of VAD's, peripheral catheters and central venous catheters. If not properly maintained, VAD's can become occluded. To ensure VAD's are used properly and do not become occluded, standards of practice have been developed. These standards include a cleaning procedure, which is commonly referred to as a flush procedure or flushing a catheter.

VAD standards of practice usually recommend flush procedures be performed after catheter placement, before fluid infusion, and before and after drug administration, blood sampling, transfusions and parenteral nutrition. The goal of these flush procedures is to confirm catheter patency, avoid drug incompatibilities, ensure the complete drug dose administration, prevent thrombus formation and minimize the risk of blood stream infections. Flush procedures require different types and amounts of flush solutions. The most commonly used flush solutions are saline and or heparin lock solution. The type of flush solution and amount vary depending on the specific type of catheter. Flush solution volumes between 5 and 10 ml are most common but can range from 1 to 20 ml. Flush procedures also require that care be taken to prevent blood reflux into the catheter. Reflux in I.V. therapy is the term commonly used to describe the fluid that is drawn back into the catheter after a flush procedure. The concern is that the reflux fluid contains blood or solution that could cause the catheter to occlude. To ensure that reflux does not occur, flush procedures suggest two techniques: 1) at the end of the flush solution delivery, the user maintains pressure on the syringe plunger while clamping the I.V. line; or 2) while delivering the last 0.5 ml of flush solution disconnect the syringe from the I.V.port or clamp the I.V. line. Either technique maintains positive pressure on the fluid in the VAD to prevent reflux of fluid and blood.

For flush procedures, the I.V. line refers to a system containing a VAD, tubing set with clamp and may terminate with a port or valve. The most common types of I.V. ports are covered by pierceable septums or pre-slit septums and are known in the art and sometimes referred to as "PRN" from the Latin pro re nata meaning "as the need arises". The septum is preferably made of rubber or another elastomeric material, which permits insertion of a sharp needle cannula in order to infuse fluids or to withdraw fluids from the catheter. Upon withdrawal of the needle cannula the septum seals itself. Ports having pre-slit septums are used with blunt cannula or the frusto-conically shaped tip of a syringe barrel. The syringe tip or the blunt cannula (which is usually attached to a syringe) is gently pushed through the pre-slit septum to establish fluid communication.

I.V. valves, another type of terminal I.V. access device that does not require a needle having a sharp tip, are activated by the frusto-conically shaped tip of a syringe barrel to allow fluid communication between the interior of the syringe and the catheter. These valves may contain structure for delivering fluid from a storage compartment in the valve to the catheter, and are referred to in the art as positive displacement valves. Such a valve is taught in U.S. Pat. No. 6,206,861B1. Positive displacement valves were developed to overcome the reflux caused by the disconnection of a syringe tip or cannula from a port or valve. Unfortunately, the positive displacement valves were not designed to compensate for the worst-case syringe stopper induced reflux. When using a traditional syringe assembly containing an elastomeric stopper, the stopper is often compressed when it contacts the distal end of the syringe barrel at the completion of the flush procedure. If the user releases the pressure on the plunger after the flush solutions is delivered, the compressed stopper may expand back to its normal size drawing fluid back into the catheter. This fluid is referred to as syringe stopper induced reflux. Traditional syringe assemblies were designed to accurately deliver medications. Traditional syringe assemblies supplied by various suppliers may appear similar but can vary significantly in terms of performance especially stopper induced reflux. Because the catheter is inserted into the patient the users cannot see the reflux when it occurs and therefore cannot take corrective actions to address a potential problem.

Disconnection induced reflux and syringe stopper induced reflux would not be an issue if all users practice the positive pressure flushing techniques described hereinabove every time they flushed a VAD. However, user experience, environmental circumstance and patient condition vary significantly within the hospital setting and even more when one considers other areas that flush procedures are performed such as clinics and home care. As a result, VAD's are frequently occluded resulting in the need for additional professional time, declotting drugs, removal of catheters and new procedures to place new catheters. All of these interventions come at a cost to the healthcare system and its patients. It is desirable to have syringe assemblies that are designed for flush procedures to enhance best clinical practice. Specifically, syringe assemblies that are configured to automatically minimize or eliminate reflux without depending entirely on user technique. Further, the prior art focuses on syringe assemblies designed to deliver medications and not syringe assemblies that automatically provide additional small amount of flush solution in the I.V. line at the completion of the flush procedure.

Therefore there is a need for a simple, straight forward, automatic, easy-to-manufacture syringe assembly which helps reduce or eliminate reflux of blood into the catheter during and after the flush procedure has occurred even if recommended flush procedure techniques are not precisely followed. For example, prematurely releasing the compressive force on the plunger and/or removing the syringe from the I.V. line before it is clamped may cause reflux of blood into the catheter, thus increasing the chance of VAD occlusion.

SUMMARY OF THE INVENTION

The present invention is directed to a syringe assembly for use in flush applications. The syringe assembly has structure to provide an additional positive displacement of flush solution after the flush solution has been substantially delivered from the cavity in the syringe barrel through the application of an additional distally-directed force provided by the stopper.

A flush syringe assembly includes a barrel having a cylindrical side wall with an inside surface defining a chamber for retaining fluid, an open proximal end and a distal end including a distal wall with a tip extending distally therefrom having a passageway therethrough in fluid communication with the chamber. A plunger including an elongate body portion having a proximal end, and a distal end is provided. A stopper is slidably positioned in fluid-tight engagement with the inside surface of the barrel for driving fluid out of the chamber by movement of the stopper relative to the barrel. The elongate portion of the plunger extends outwardly from the open proximal end of the barrel. The plunger includes a discontinuity for engaging the barrel for stopping the distal motion of the plunger before the stopper fully delivers all of the liquid in the chamber. The stopper includes a proximal stopper portion connected to the distal end of the plunger and a distal stopper portion separated from the proximal stopper portion by spring means for moving the distal stopper portion in a distal direction to drive more of the liquid out of the chamber after the discontinuity on the plunger engages the barrel to stop the distal motion of the plunger. Spring means may be any spring element which deflects under force and expand when the force is removed or reduced, such as a coil spring, a pocket of air between the distal and proximal stopper portions, or any element configured to act as a spring such as an annular cantilevered element. The syringe assembly may include a distal stopper portion which is configured to engage the inside surface of the barrel so that less force is required to move the distal stopper portion along the chamber than to move the proximal stopper portion along the chamber. This configuration favors movement of the distal stopper portion when the spring element expands between the two stopper portions.

The syringe assembly may include a distal stopper portion having at least one circumferential sealing rib engaging the inside surface of the barrel and said proximal stopper portion having at least two circumferential sealing ribs engaging the inside surface of the barrel.

The syringe assembly may be configured so that the discontinuity on the plunger is configured to engage a discontinuity on the barrel to retain the plunger and prevent further distal and proximal motion of the plunger with respect to the barrel during normal use of the syringe assembly.

The syringe assembly may be configured so that deflection of the spring element desirably occurs when the liquid pressure in the chamber is about 5 mm Hg (0.1 psi) or more.

When the syringe assembly of the present invention is attached to a peripheral catheter the amount of fluid moving distally in the passageway after distal motion of the plunger with respect to the barrel has stopped, is about 0.001 ml or more.

It is also desirable that the desired volume of additional fluid, when the syringe assembly is connected to a peripheral catheter, be delivered in a time of 0.5 second or more. It is preferable that the additional fluid be delivered in a time of about 2.5 seconds or more.

The syringe assembly may further include structure for allowing air trapped between the proximal stopper portion and the distal stopper portion to escape toward the open proximal end of the barrel. This structure may include an aperture in the plunger, a less than air-tight fit between the plunger and the proximal stopper portion and/or a discontinuity in the outside diameter of said proximal stopper portion.

The syringe assembly may further have a needle assembly attached thereto. The needle assembly includes a cannula having a proximal end, a distal end and a lumen therethrough, and a hub having an open proximal end containing a cavity and a distal end attached to the proximal end of the cannula so that the lumen is in fluid communication with the cavity. The needle assembly is removably attached to the tip of the barrel to engagement of the tip to the cavity in the hub so that the lumen is in fluid communication with the barrel chamber.

BRIEF DESCRIPTION OF THE DRAWINGS

FIG. 8 is side-elevational view of an alternative stopper of the present invention.

FIG. 9 is a cross-sectional view of the stopper of FIG. 8 taken along line 9-9.

DETAILED DESCRIPTION

Figure 1:
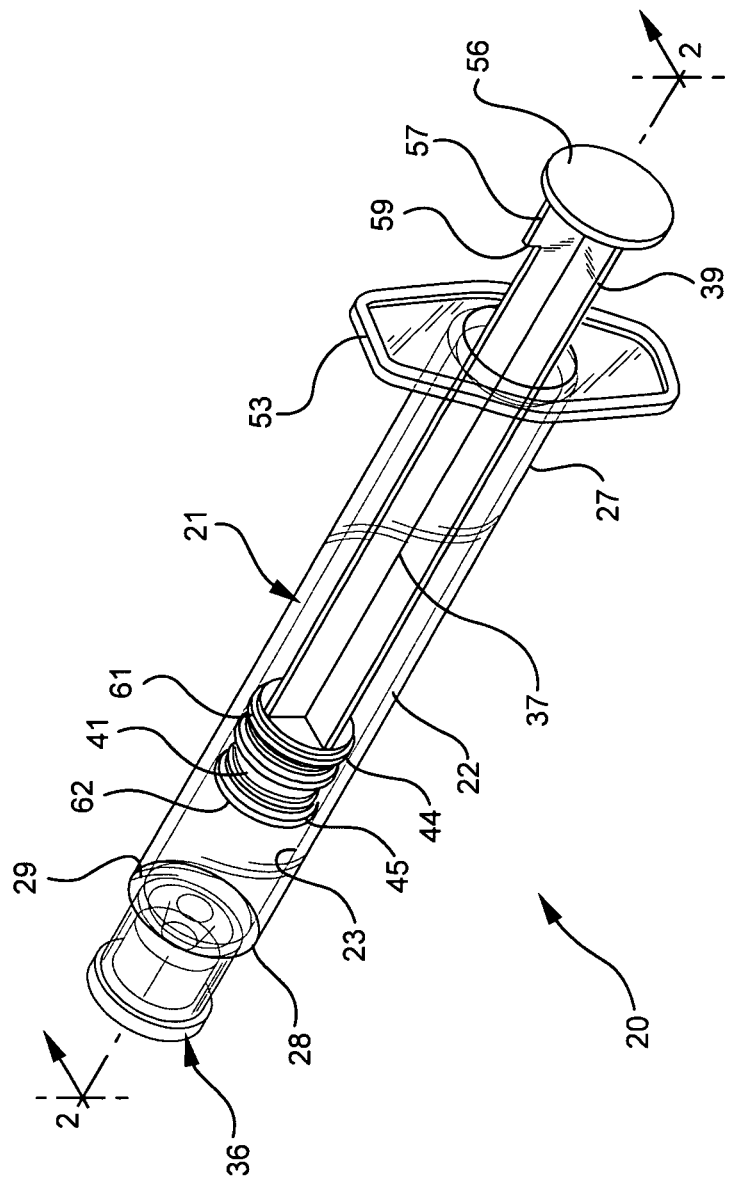
FIG. 1 is a perspective view of the syringe assembly of the present invention.
Figure 2:
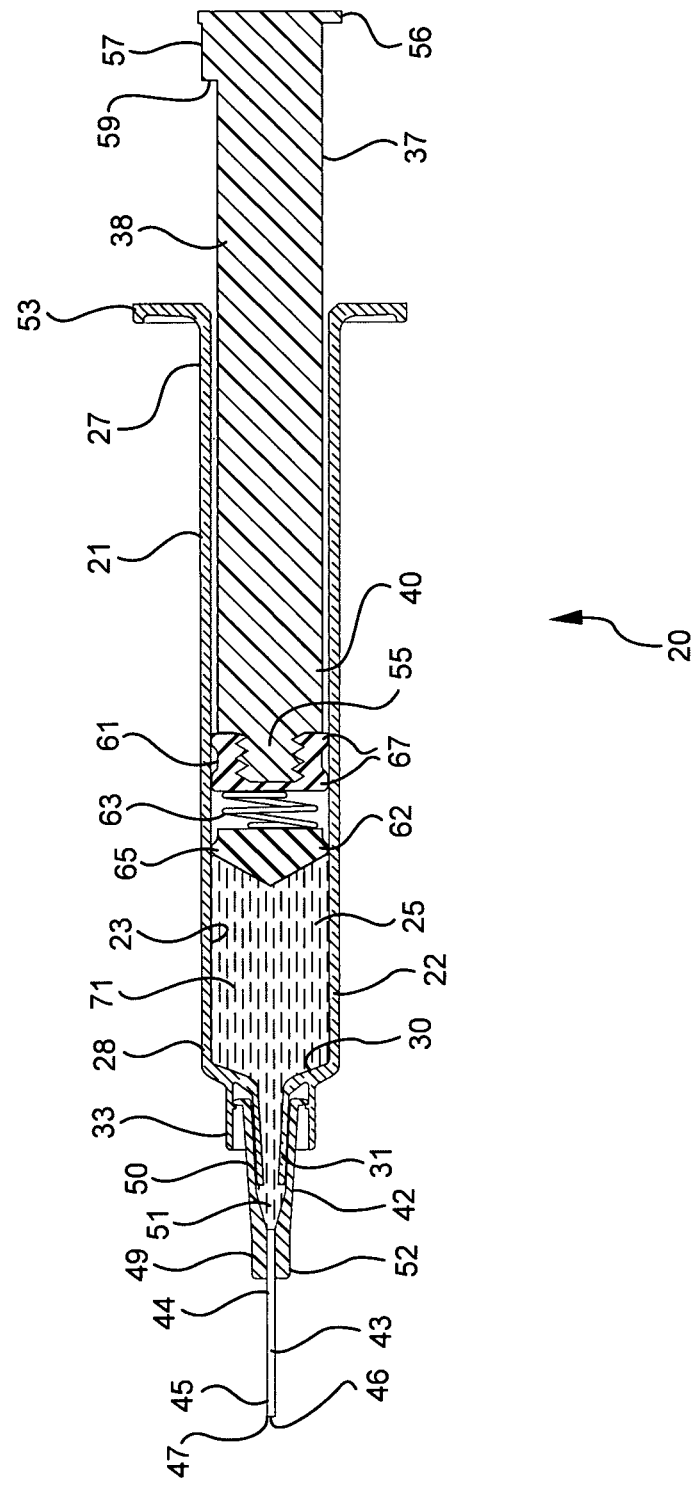
FIG. 2 is an enlarged partially cross-sectioned side-elevation view of the syringe assembly of FIG. 1 with a needle assembly attached.

Referring to FIGS. 1-7, a syringe assembly 20 according to the present invention generally comprises a barrel 21, including a cylindrical sidewall 22 having an inside surface 23 defining a chamber 25 for retaining fluid. The barrel further includes an open proximal end 27 and a distal end 28 having a distal wall 29 with an elongate tip 31 extending distally therefrom and having a passageway 32 therethrough in fluid communication with the chamber. The inside surface of the barrel at the distal wall, indicated as 30, is preferably conically shaped. The distal end of the barrel preferably, but not necessarily, includes a locking luer type collar 33 concentrically surrounding tip 31. The collar includes an inside surface 34 having at least one thread 35 thereon.

A cannula 43 includes a proximal end 44, a distal end 45 and a lumen 46 therethrough. The distal end of the cannula may include a sharp tip or a blunt tip 47 as shown. The cannula may be connected directly to the tip of the syringe barrel to establish fluid communication between the lumen and the chamber. Also, the cannula may be part of a needle assembly 42 including a hub 49 having an open proximal end 50 containing a cavity 51 and a distal end 52 attached to the proximal end of the cannula so that lumen of the cannula is in fluid communication with the cavity. The cavity of the hub can be removably frictionally engaged to the tip of the barrel.

A plunger 37 includes an elongate body portion 38, a proximal end 39 and a distal end 40. A stopper 41 is disposed at the distal end of the plunger rod through a structure that will be described in more detail hereinafter. The stopper is slidably positioned in fluid-tight engagement with the inside surface of the barrel for drawing fluid into and driving fluid out of the chamber by movement of the stopper relative to the barrel. If the syringe assembly is prefilled from the manufacturer, the stopper need not be used for or able to draw fluid into the barrel. Elongate body portion of the plunger extends outwardly from the open proximal end of the barrel.

Syringe assembly 20 includes a discontinuity on the plunger for engaging the barrel for stopping the distal motion of the stopper before it fully delivers all of the liquid from the chamber. In this embodiment the discontinuity comprises radial projection 57 on the plunger having a distal surface 59 for contacting the barrel to stop the distal motion of the plunger before the stopper fully delivers all of the liquid in the chamber. There are numerous structures for limiting the distal motion of the plunger with respect to the barrel including any combination of discontinuities such as projections or recesses on the barrel and/or the plunger. For example; a plunger flange 56 can contact finger grips 53 at the proximal end of the barrel to limit plunger motion. All of these possibilities are within the purview of the present invention and the radial projection on the plunger in this embodiment is merely representative of these many possibilities.

Stopper 41 includes a proximal stopper portion 61 connected to the distal end of the plunger and the distal stopper portion 62 separated from the proximal stopper portion by spring means for moving the distal stopper portion in a distal direction to drive more of the liquid out of the chamber after radial projection 57 engages the barrel to stop the distal motion of the plunger. In this embodiment, spring means includes a coil spring 63.

In this embodiment, the stopper and the plunger are connected through the action of an external thread 58 on the distal end of the plunger and internal thread 64 in the proximal stopper portion. There are numerous ways to connect the stopper and plunger, including a snap-fit arrangement, adhesives, fasteners, ultrasonic welding, two stage molding and the like. The end of the plunger can engage the exterior of the stopper rather than the interior or just the proximal end of the stopper. All of these various structures for connecting a stopper to a plunger are within the purview of the present invention and the threaded engagement described in this embodiment is merely illustrative of these many possibilities. In this embodiment distal surface 63 of the stopper is conically shaped and inside surface 23 of barrel 21 at distal wall 29 is also conically shaped.

The stopper may be made of any material suitable for providing sealing characteristics while under compression. For example, the stopper may be made of thermoplastic elastomers, natural rubber, synthetic rubber or thermoplastic materials and combinations thereof. The stopper may be integrally formed or composed of separate components of the same or different materials joined together. The plunger in this embodiment is preferably made of material which is more rigid than the stopper such as polypropylene, polyethylene and the like. Materials should be chosen to be compatible with the sterilization procedure being used.

In operation, syringe assembly 20 is connected to a needle assembly and filled with flush solution using known methods. Also, the syringe assembly may be provided pre-filled from the manufacturer or supplier. The flush solution may be any solution intended for flushing or maintaining the performance of VAD's. It is preferred that the flush solution be selected from the group consisting of saline flush solution and heparin lock flush solution. These solutions are known in the art and readily available. An example of a saline flush solution is 0.9% Sodium Chloride USP for injection. An example of a heparin lock flush solution is 0.9% Sodium Chloride with 100 USP units of Heparin Sodium per ml or 10 USP units of Heparin Sodium per ml. The syringe with needle assembly attached is used to pierce the pierceable septum or a blunt cannula may be inserted into a pre-split septum of a vial or neck of a glass ampoule containing flush solution and the flush solution is drawn into the syringe barrel by pulling plunger flange 56 in the proximal direction while holding barrel 21, to draw fluid through the needle cannula into fluid chamber 25.

Alternatively, large quantities of flush syringes may be pre-filled with flush solution during or after the assembly of the syringe using sterile filling methods. Such prefilled syringes may be supplied with a tip cap, such as tip cap 36 releasably connected to tip 31 sealing passageway 32. It is preferred that the tip cap is formed of material selected from a group of thermoplastic materials and elastomeric materials such as natural and synthetic rubber, thermoplastic elastomers or combinations thereof.

Figure 6:
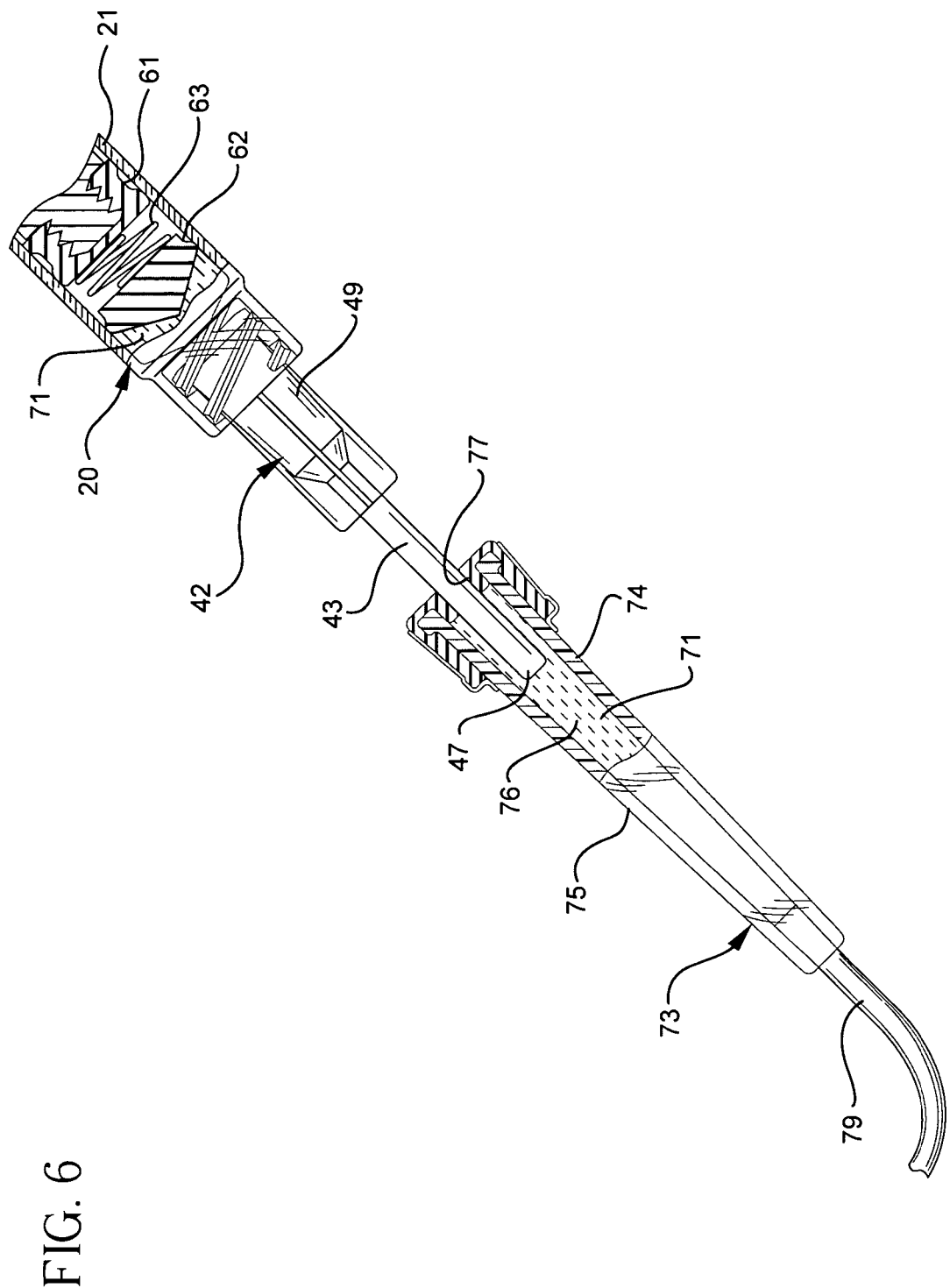
FIG. 6 is a side-elevational view illustrating the syringe assembly in use with a catheter injection site.

The syringe is now ready for use in flushing a VAD such as a catheter of an I.V. set. I.V. sets can be very complicated and may include multiple injection ports, a valve and/or other components. For the purpose of illustrating the present invention a simplified I.V. set 73 is illustrated in FIG. 6. I.V. set 73 comprises an I.V. site 74 which includes a housing 75 having a hollow interior 76 and a septum 77 at its proximal end. An I.V. line 79 having a conduit therethrough extends from the distal end of the housing. I.V. line 79 may be a catheter or connected to a catheter at its distal end. For this I.V. set, septum 77 is pre-slit for use with blunt cannula. The I.V. site may be a valve having structure for accepting the syringe barrel tip and being activated by the insertion of the tip to establish fluid communication with the catheter, such as the valve taught in U.S. Pat. No. 6,171,287.

As previously mentioned, there are two general classifications of VAD's, peripheral catheters and central venous catheters. Peripheral catheters are used to access veins in the peripheral extremities such as the hand and arm. Peripheral catheters are relatively short in length ranging from about 14 mm to 48 mm in length, and are available in gauge sizes from about 16 to 24. It is believed that the most commonly used peripheral catheters are 20 gauge having an ID of about 0.81 mm (0.032 inch) and 22 gauge having an ID of about 0.66 mm (0.026 inch), and having a length of about 25 mm to 32 mm. As used herein, the term "peripheral catheter" is intended to refer to a 20 or 22 gauge catheter having a length of about 25 mm. Central venous catheters are substantially longer than peripheral catheters and are inserted in the patient and terminate near the heart.

Blunt tip 47 of cannula 43 may be inserted through pre-slit septum 77 of I.V. set 73. Alternatively, a sharp tip of a needle cannula may be used to pierce a septum that is not pre-slit, or the tip of the barrel may be engaged with a valve in the IV site. This establishes fluid communication between the interior 76 of the I.V. set and the chamber of the syringe barrel. The syringe barrel 21 is preferably held via finger grips 53. Pressure is then applied to flange 56 of the plunger, for example by a thumb, in the distal direction. This moves plunger 37 having stopper 41 on its distal end forcing the liquid such as flush solution 71 in chamber 25 out of the chamber, through cannula 43 and into interior 76 of the I.V. set and then through I.V. line 79.

Figure 3:
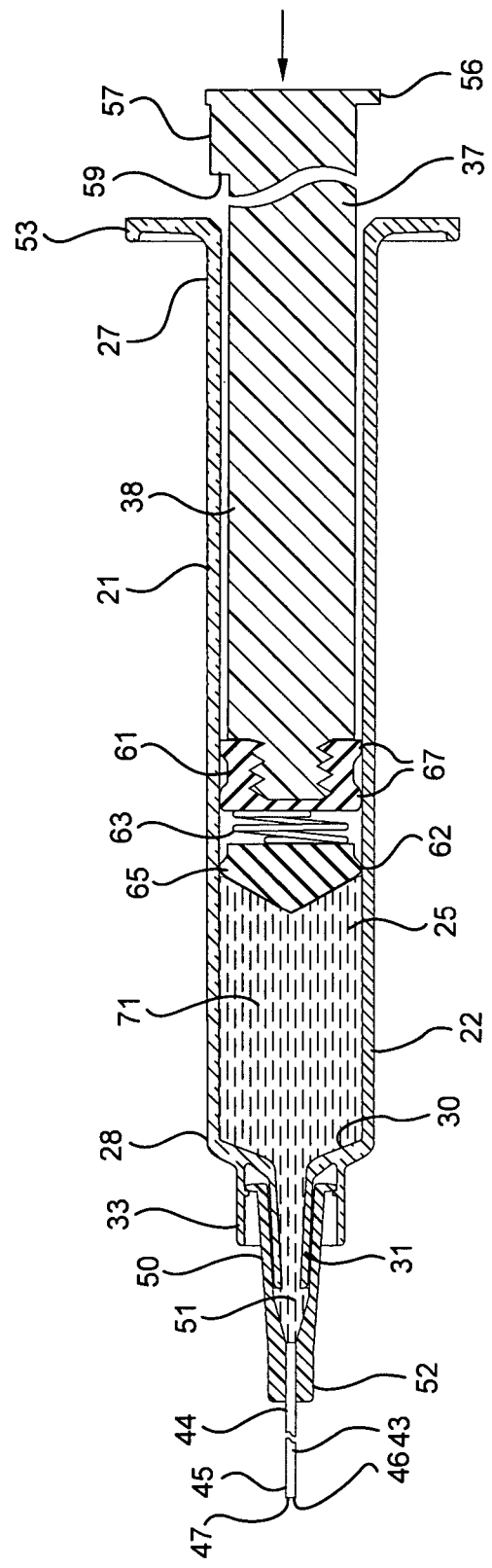
FIG. 3 is an enlarged partial cross-sectional side-elevation view of the syringe assembly of FIG. 2 shown during the flush procedure.

FIG. 3 illustrates syringe assembly 20 during a flush procedure wherein force F is being applied to flange 56 of the plunger forcing flush solution 71 from the chamber through passageway 32 and through the lumen of the cannula, through a catheter and into the patient's vein. It should be noted that the pressure on the flush solution during the flush procedure is higher than the patient's blood pressure where the catheter enters the blood vessel, so that fluid moves into the catheter. This higher pressure causes distal stopper portion 62 to deflect spring 63 and move closer to proximal stopper portion 61 while the plunger is being advanced in a distal direction within the barrel. It is desired that the spring will deflect under fluid pressure in the barrel of about 5 mm Hg. (0.1 psi) or more. It is preferred that the spring will deflect enough during the flush procedure to allow delivery of an additional 0.001 ml or more of liquid when the flush procedure is completed. When connected to a peripheral catheter, it is also desirable that the spring will deliver the desired amount of liquid within 0.5 seconds or more seconds after the completion of the flushing caused by the distal motion of the plunger with respect to the barrel. A spring configured to compress under fluid pressure of about 5 mm Hg (0.1 psi) or more and to force about 0.001 ml or more of liquid into a catheter after a flush procedure, in 0.5 seconds or more is desirable. However, a wide variation in these pressure, displacement and volume parameters can be used to accomplish the desired result. The parameters chosen may depend on the configuration and placement of the VAD, the syringe size and the flush solution being used.

Figure 4:
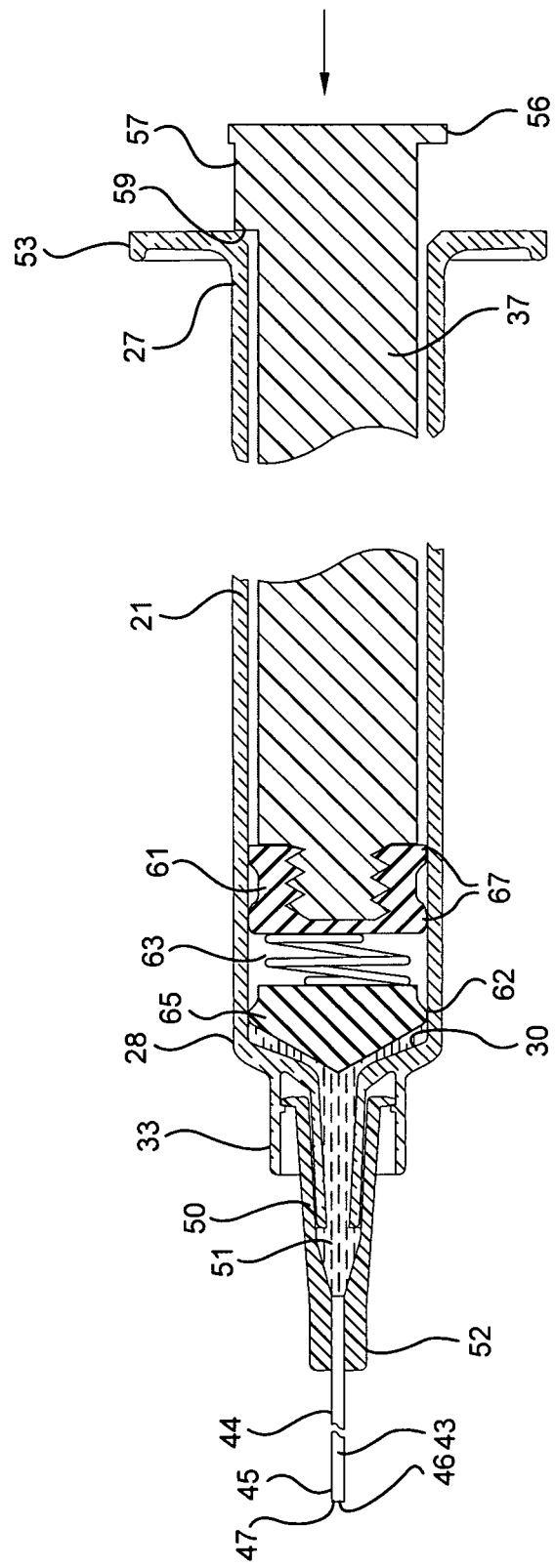
FIG. 4 is an enlarged partial cross-sectional side-elevation view of the syringe assembly shown at the completion of the flush solution delivery.
Figure 5:
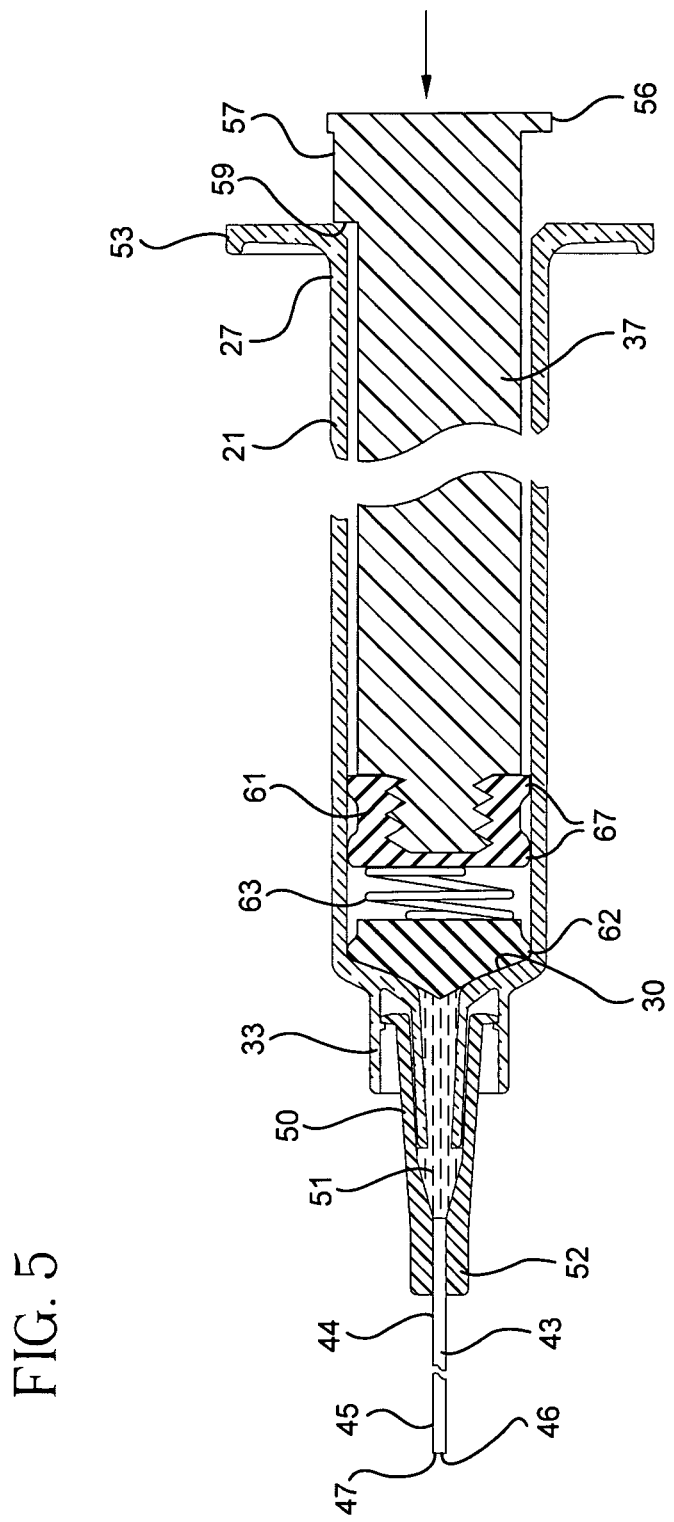
FIG. 5 is an enlarged partially cross-sectional side-elevational view of the syringe assembly shown after the completion of flush solution delivery and after the stopper has driven an additional amount of flush solution through the syringe barrel passageway.

Referring to FIG. 4, the position of the plunger and the stopper at the completion of the flush procedure is shown. At the completion of the flush procedure distal motion of the plunger relative to the barrel has been stopped by contact of projection 57 and the barrel. This contact is made before all of the liquid in the chamber has been delivered. At this point, while the user is clamping the I.V. line, distal stopper portion 62 is moving back toward its original position with respect to proximal stopper portion 61 by action of spring 63 which has been compressed during the flush procedure, as illustrated in FIG. 5, and in doing so is forcing additional I.V. solution out of the chamber and through the passageway of the barrel.

The positive displacement of fluid in the passageway in a distal direction will help prevent reflux while the I.V. line is being clamped and the syringe is being removed. After the I.V. line is clamped, the syringe assembly may be removed from the I.V. set. It should be noted that removing a syringe from an I.V. set can promote reflux by the withdrawal of solid elements of the syringe and/or cannula from a closed system. This potential withdrawal reflux can be compensated for by the positive displacement of flush solution by the stopper in the syringe assembly of the present invention.

Figure 7:
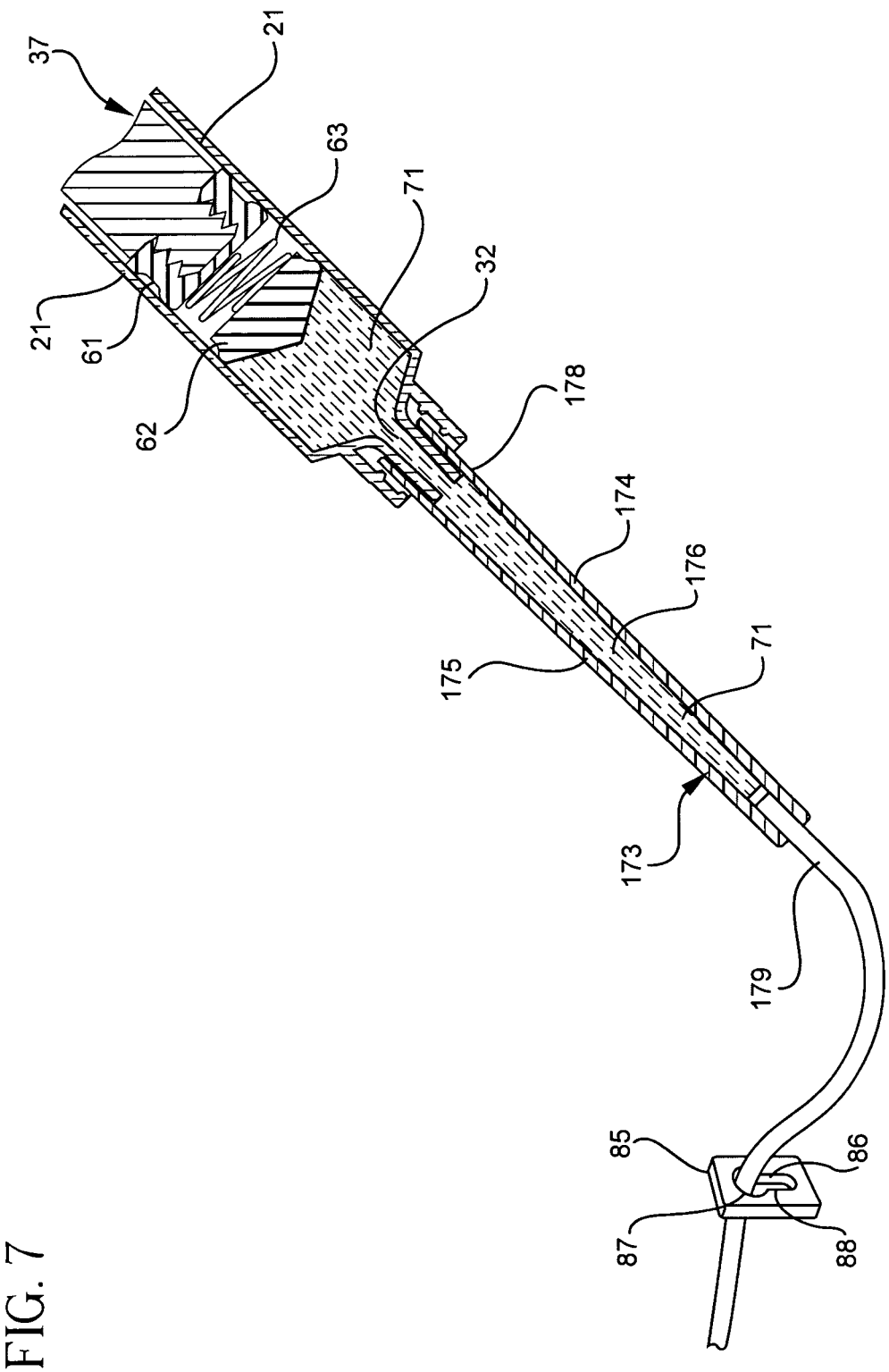
FIG. 7 is a side-elevational view illustrating the syringe assembly in use with another catheter injection site.

FIG. 7 shows an alternative simplified I.V. set to illustrate a flush procedure without a needle assembly. In FIG. 7, I.V. set 173 comprises an I.V. site 174 which includes a housing 175 having a hollow interior 176 and a luer fitting 178 at its proximal end. An I.V. line 179 having a conduit therethrough extends from the distal end of the housing. The I.V. line may be a catheter or connected to a catheter at its distal end. The I.V. set illustrated in FIG. 7 is simplified to demonstrate the invention. In most cases a luer fitting such as luer fitting 178 would be part of a one-way valve in the I.V. set. The elongate tip of the barrel is inserted and engaged with the luer fitting to establish fluid communication between interior 176 of the I.V. set and the chamber of the syringe barrel. Pressure is then applied to a flange on the proximal end of the plunger, for example by a thumb, in the distal direction. This moves plunger 37 having stopper 41 on its distal end, forcing liquid such as flush solution 71 in chamber 25 out of the chamber, through passageway 32 in the elongate tip into hollow interior 176 of the I.V. set and then through I.V. line 179. The remainder of the flush procedure is substantially identical to the procedures described when using I.V. set 73 of FIG. 6. One way to clamp an I.V. line is through the use of locking member 85 which is a thin element usually made of plastic having a slot 86 therein. The slot has an enlarged portion 87 which allows flow through the I.V. line and a narrow portion 88. At the completion of the flush procedure the I.V. line is forced into the narrow portion of the slot which compresses the I.V. line to a closed configuration. Based on the experience of the person performing the flush procedure and the clinical circumstances at the time of the procedure, e.g. the patient is in an agitated state, it may be difficult to clamp the line with one hand while holding the syringe with the other hand. The present invention can allow the user to momentarily release the syringe and use two hands to clamp the I.V. line because of the syringe is still exerting a positive pressure on the flush solution as the distal wall of the stopper moves back toward its original shape.

Another feature of the present invention is that the distal stopper portion may be configured to engage the inside surface of the barrel so that less force is required to move the distal stopper portion along the chamber than the force required to move the proximal stopper portion. There are many ways to accomplish this result including having more annular ribs on the proximal stopper portion than on the distal stopper portion or having a larger diameter proximal stopper portion to increase the friction between the barrel and the proximal stopper portion. Also different materials, having different coefficients of friction or different surface configurations may be used to make the distal stopper portion move more easily in the barrel than proximal stopper portion. This feature is preferred because it can allow the user to momentarily release the distally-directed pressure on the plunger at the completion of the flush procedure since expanding spring will tend to move the distal stopper portion forward rather than moving the proximal stopper portion in a rearward or proximal direction. In the present embodiment distal stopper portion 62 has one annular sealing rib 65 and proximal stopper portion 61 has two (2) annular sealing ribs 67.

FIGS. 8 and 9 illustrate an alternative embodiment of the stopper of the present invention. In this embodiment stopper 141 includes proximal stopper portion 161 having an annular sealing rib 167 and an internal thread 164 for engaging a plunger. A distal stopper portion 162 having an annular sealing rib 165 is separated from the proximal stopper portion by spring element 163 provided for moving the distal stopper portion in a distal direction to drive liquid out of the chamber of a syringe barrel after the proximal stopper portion stops moving in the distal direction. The stopper in this embodiment functions similarly to the stopper in the embodiment of FIGS. 1-7. Spring element 163 is a cantilevered annular element comprising an outwardly diverging frusto-conically shaped portion 168 and an inwardly converging frusto-conically shaped portion 169. The fluid pressure in the chamber will deflect the annular cantilevered element during a flush procedure and afterward the energy in the annular cantilevered element will urge the distal stopper portion to its original position with respect to the proximal stopper portion.

Figure 11:
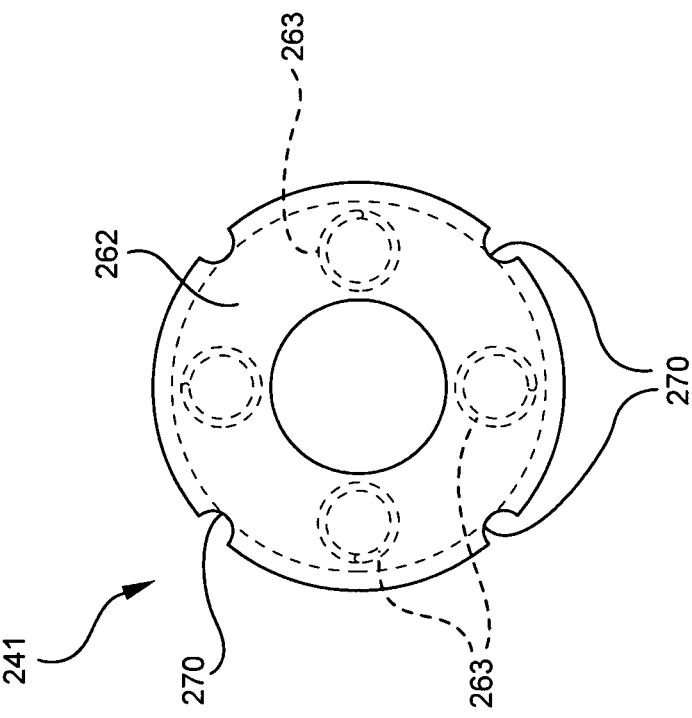
FIG. 11 is a bottom-plan view of the stopper of FIG. 10.
Figure 10:
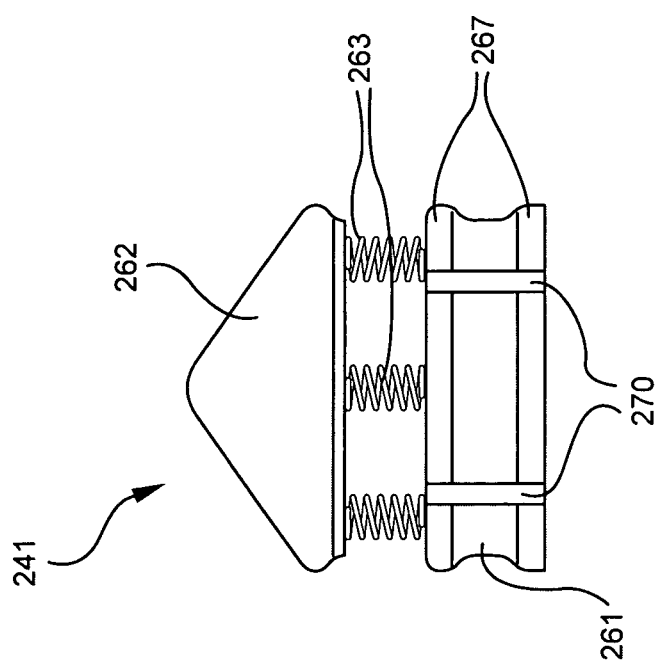
FIG. 10 is a side-elevational view of another alternative stopper of the present invention.

FIGS. 10 and 11 illustrate another alternative stopper of the present invention. In this embodiment stopper 241 includes a proximal stopper portion 261 having annular sealing ribs 267 and a distal stopper portion 262 separated from the proximal stopper portion by spring elements 263. Stopper 241 functions similarly to the stopper of the embodiments of FIGS. 1-7. In addition stopper 241 includes one or more axial grooves 270 cutting through annular sealing ribs 267. In order to more carefully control the forces from which spring element 263 compresses and expands, it may be desirable to remove trapped air between the distal stopper portion and the proximal stopper portion. Since the air would also act as a spring element. With the air vented toward the open proximal end of the barrel, the primary determiner of the spring element force will be the spring element itself and the frictional relationship between the stopper portions and the inside of the barrel. It should also be noted that without a means of allowing air trapped between the proximal portion and the distal portion of the stopper to escape toward the open proximal end of the barrel, the air alone, without a mechanical spring can comprise a spring element. Air trapped between the proximal stopper portion and the distal stopper portion can also be allowed to escape by having a less than air-tight fit between the plunger and the proximal stopper portion and/or by having an aperture in the distal end of the plunger.

Figure 13:
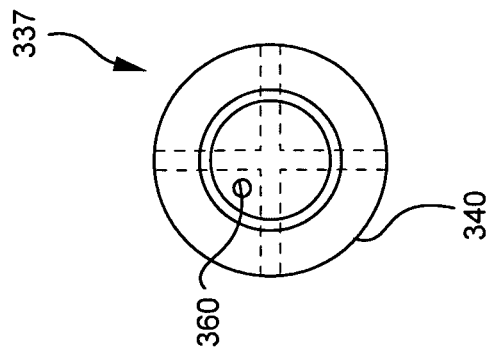
FIG. 13 is an end plan view of the plunger of FIG. 12.
Figure 12:
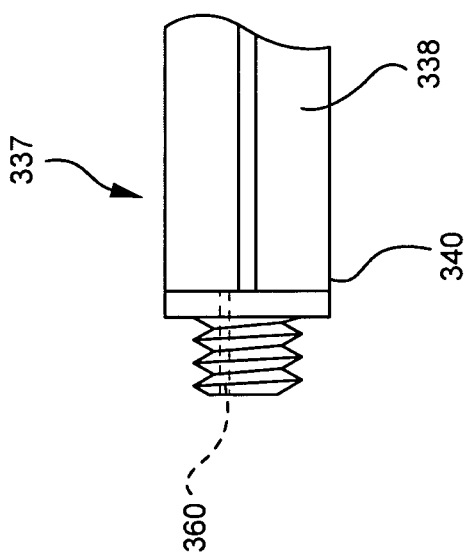
FIG. 12 is a partial side-elevational view of the distal end of an alternative plunger of the present invention.

FIGS. 12 and 13 illustrate an alternative plunger of the present invention. In this embodiment, plunger 337 includes an elongate body portion 338 having a distal end 340 with aperture 360 therethrough. Aperture 360 allows air trapped between the distal stopper portion and the proximal stopper portion, in some embodiments, to escape into the chamber and out of the open proximal end of the barrel.

Figure 14:
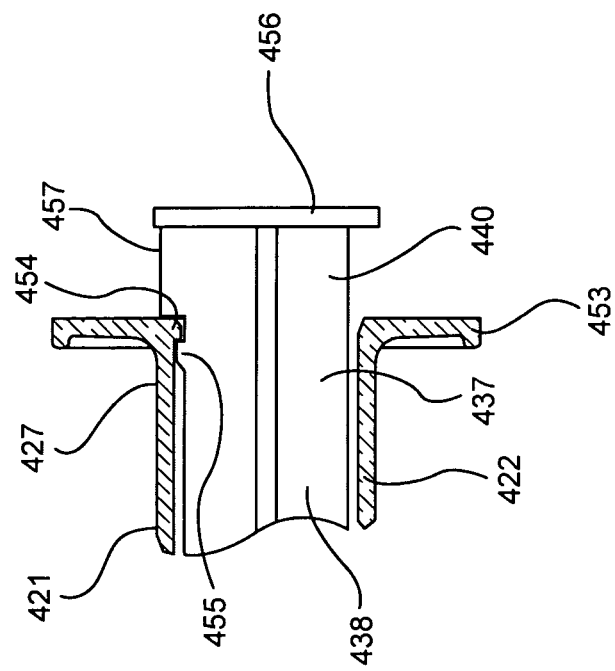
FIG. 14 is a partial, partially-cross-sectioned side-elevation view of an alternative barrel and plunger of the present invention.

FIG. 14 illustrates an alternative barrel and plunger of the present invention. In this embodiment a barrel 421 includes a cylindrical side wall 422, an open proximal end 427 and finger grips 453 on the proximal end. The barrel also includes an inwardly directed annular projection 454. Plunger 437 includes an elongate body portion 438 having a proximal end 440 including a proximal flange 456 and a radial projection 457.

In use, radial projection 457 on the plunger engages the barrel for stopping distal motion of the plunger before the stopper fully delivers all of the liquid from the chamber. In addition, in this embodiment, secondary radially directed projection 455 on the plunger will snap past annular projection 454 at the completion of the flush procedure. The interaction of radial projections 455 and 457 on the plunger and annular projection 454 in the barrel act to retain the plunger and prevent further distal and proximal motion of the plunger with respect to the barrel during normal use of the syringe assembly. There are many combinations of discontinuities on the plunger and/or the barrel for retaining the plunger to prevent further distal and proximal motion, and the structure of the embodiment of FIG. 14 is merely representative of these many possibilities.

What is claimed is:

1. A flush syringe assembly for reducing reflux of blood into a vascular access device during and after a flush procedure comprising:
    a barrel including a cylindrical side wall having an inside surface defining a chamber for retaining fluid, an open proximal end having an inwardly directed annular projection and a distal end including a distal wall with a tip extending distally therefrom having a passageway therethrough in fluid communication with said chamber;
    a plunger including an elongate body portion having a proximal end having a radially directed projection and a secondary radially directed projection, and a distal end, a stopper slidably positioned in fluid-tight engagement with said inside surface of said barrel for driving fluid out of said chamber by movement of said stopper relative to said barrel, said elongate body portion extending outwardly from said open proximal end of said barrel, the radially directed projection on the proximal end of the plunger and the secondary radially directed projection positioned to snap past the inwardly directed annular projection on the proximal end of the barrel to retain the plunger and to prevent further distal and proximal motion of the plunger with respect to the barrel;
    a discontinuity including an outwardly directed fixed radial projection on said elongate body portion on said plunger having a distal surface extending beyond the cylindrical side wall of the barrel for direct engagement of the plunger with said barrel for stopping the distal motion of said plunger before said stopper fully delivers all liquid from said chamber,
    said stopper including a proximal stopper portion connected to said distal end of said plunger and a distal stopper portion separated from said proximal stopper portion by a spring for moving said distal stopper portion in a distal direction to drive more liquid out of said chamber after said discontinuity on said plunger engages said barrel to stop distal motion of said plunger, wherein said distal stopper portion has at least one circumferential rib engaging said inside surface of said barrel and said proximal stopper portion has at least two circumferential ribs engaging said inside surface of said barrel to engage said inside surface of said barrel so that less force is required to move the distal stopper portion along said chamber than said proximal stopper portion.

2. The syringe assembly of claim 1 wherein said spring element includes a coil spring.

3. The syringe assembly of claim 1 wherein said spring is an annular cantilevered element.

4. The syringe assembly of claim 1 wherein said spring includes an air space between said distal stopper portion and said proximal stopper portion.

5. The syringe assembly of claim 1 wherein said discontinuity on said plunger is configured to engage a discontinuity on said barrel to retain the plunger and prevent further distal and proximal motion of said plunger with respect to said barrel during normal use of said syringe assembly.

6. The syringe assembly of claim 1 wherein said plunger defines an aperture for allowing air trapped between said proximal stopper portion and said distal stopper portion to escape toward said open proximal end of said barrel.

7. The syringe assembly of claim 1 wherein there is a less than air-tight fit between said plunger and said proximal stopper portion for allowing air trapped between said proximal stopper portion and said distal portion to escape toward said open proximal end of said barrel.

8. The syringe assembly of claim 1 wherein an outside diameter of said proximal stopper portion includes at least one discontinuity for allowing air trapped between said proximal stopper portion and said distal portion to escape toward said open proximal end of said barrel.

9. The syringe assembly of claim 1 wherein deflection of said spring occurs when said liquid pressure is about 5 mm Hg. (0.1 psi) or more.

10. The syringe assembly of claim 1 including flush solution in said chamber.

11. The syringe assembly of claim 10 wherein said flush solution is selected from the group consisting of saline flush solution and heparin lock flush solution.

12. The syringe assembly of claim 10 further including a tip cap releasably connected to said tip of said syringe barrel for sealing said passageway.

13. The syringe assembly of claim 1 wherein said stopper is made of material selected from the list consisting of thermoplastic elastomers, natural rubber, synthetic rubber, thermoplastic materials and combinations thereof.

14. The syringe assembly of claim 1 further comprising a needle assembly including a cannula having a proximal end, a distal end and a lumen therethrough, and a hub having an open proximal end containing a cavity and a distal end attached to said proximal end of said cannula so that said lumen is in fluid communication with said cavity, said needle assembly being removably attached to said tip of said barrel through engagement of said tip to said cavity so that said lumen is in fluid communication with said chamber.

15. The syringe assembly of claim 1, wherein a single user can engage the discontinuity with the barrel to prevent distal motion of the plunger using one or two hands.

* * * * *